United States Patent
Schuessler et al.

(10) Patent No.: US 8,043,373 B2
(45) Date of Patent: Oct. 25, 2011

(54) ALL-BARRIER ELASTOMERIC GEL-FILLED BREAST PROSTHESIS

(75) Inventors: David J. Schuessler, Ventura, CA (US); Thomas E. Powell, Santa Barbara, CA (US)

(73) Assignee: Allergan, Inc., Irvine, CA (US)

( * ) Notice: Subject to any disclaimer, the term of this patent is extended or adjusted under 35 U.S.C. 154(b) by 200 days.

(21) Appl. No.: 12/179,340

(22) Filed: Jul. 24, 2008

(65) Prior Publication Data
US 2009/0030515 A1 Jan. 29, 2009

Related U.S. Application Data

(60) Provisional application No. 60/952,304, filed on Jul. 27, 2007.

(51) Int. Cl.
*A61F 2/12* (2006.01)

(52) U.S. Cl. ............................................................ 623/8

(58) Field of Classification Search .................... 623/7–8
See application file for complete search history.

(56) References Cited

U.S. PATENT DOCUMENTS

| | | | |
|---|---|---|---|
| 4,455,691 A * | 6/1984 | Van Aken Redinger et al. . | 623/8 |
| 4,592,755 A | 6/1986 | Penton et al. | |
| 4,650,487 A * | 3/1987 | Chaglassian | 623/8 |
| 4,773,909 A | 9/1988 | Chaglassian | |
| 5,534,609 A * | 7/1996 | Lewis et al. | 528/15 |
| 6,074,421 A | 6/2000 | Murphy | |
| 6,099,565 A * | 8/2000 | Sakura, Jr. | 623/8 |
| 6,602,452 B2 | 8/2003 | Schuessler | |
| 7,165,964 B2 | 1/2007 | Schuessler | |
| 2003/0163197 A1 * | 8/2003 | Chen | 623/7 |
| 2010/0049317 A1 * | 2/2010 | Schuessler | 623/8 |

FOREIGN PATENT DOCUMENTS

| | | |
|---|---|---|
| EP | 029 292 B1 | 5/1981 |
| EP | 030 838 B1 | 6/1981 |

* cited by examiner

*Primary Examiner* — Suzette J Gherbi
(74) *Attorney, Agent, or Firm* — Linda A. Fox; Stephen Donovan; Debra Condino

(57) ABSTRACT

An elastomeric gel-filled prosthetic implant having a shell made of a single gel barrier layer. The barrier layer is formed of a homogeneous silicone elastomer capable of sterically retarding permeation of the silicone gel through the shell and having a bleed rate that is less than about 40% of the bleed rate of current shells which use a sandwiched construction with an internal barrier layer. Further, the barrier layer shell is made of a material that exhibits a wet strength that is comparable to or greater than current shells. The silicone elastomer may be a polydimethyl siloxane, and the substituted chemical group is a diphenyl group with a minimum mole percent of at least 13%. The implant may be designed for breast reconstruction or augmentation such that the shell is accordingly shaped. The shell wall thickness is at least 0.254 mm (0.010 inches), and desirably about 0.456 mm (0.018 inches). The implant shell may be made by dip-forming, spray-forming, or rotational molding. The exterior may be smooth or textured.

24 Claims, 7 Drawing Sheets

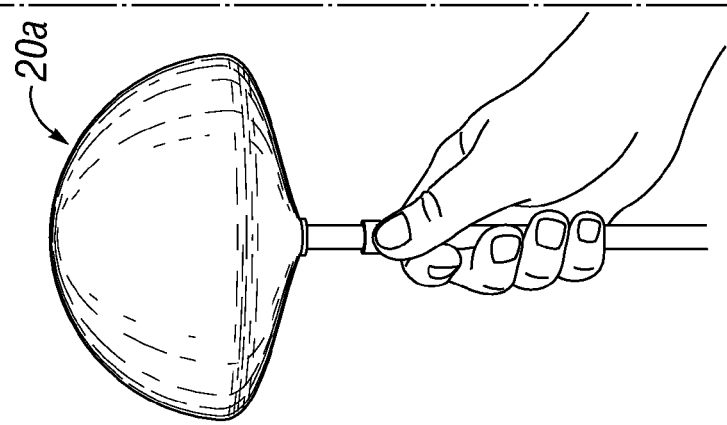
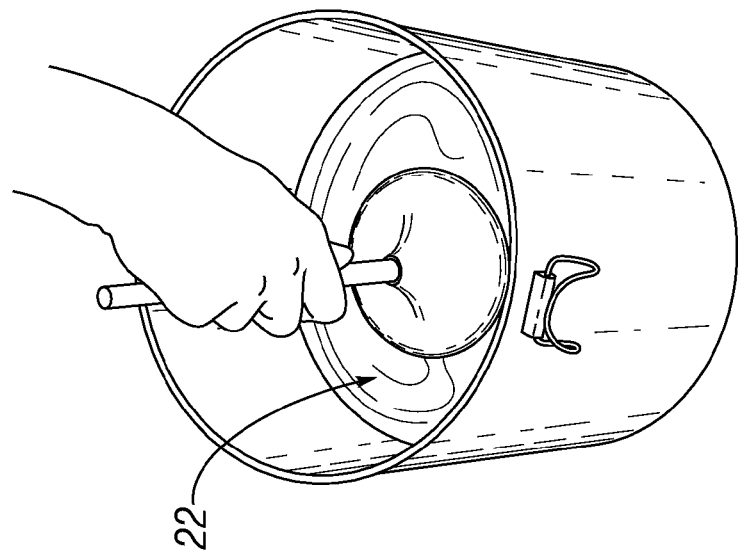
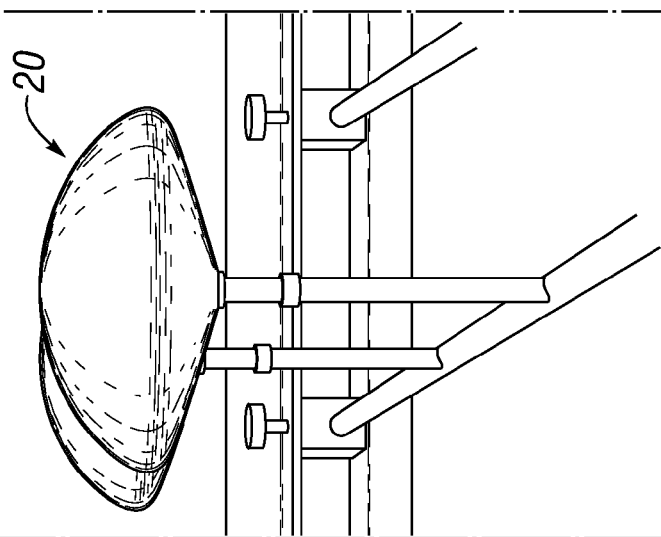

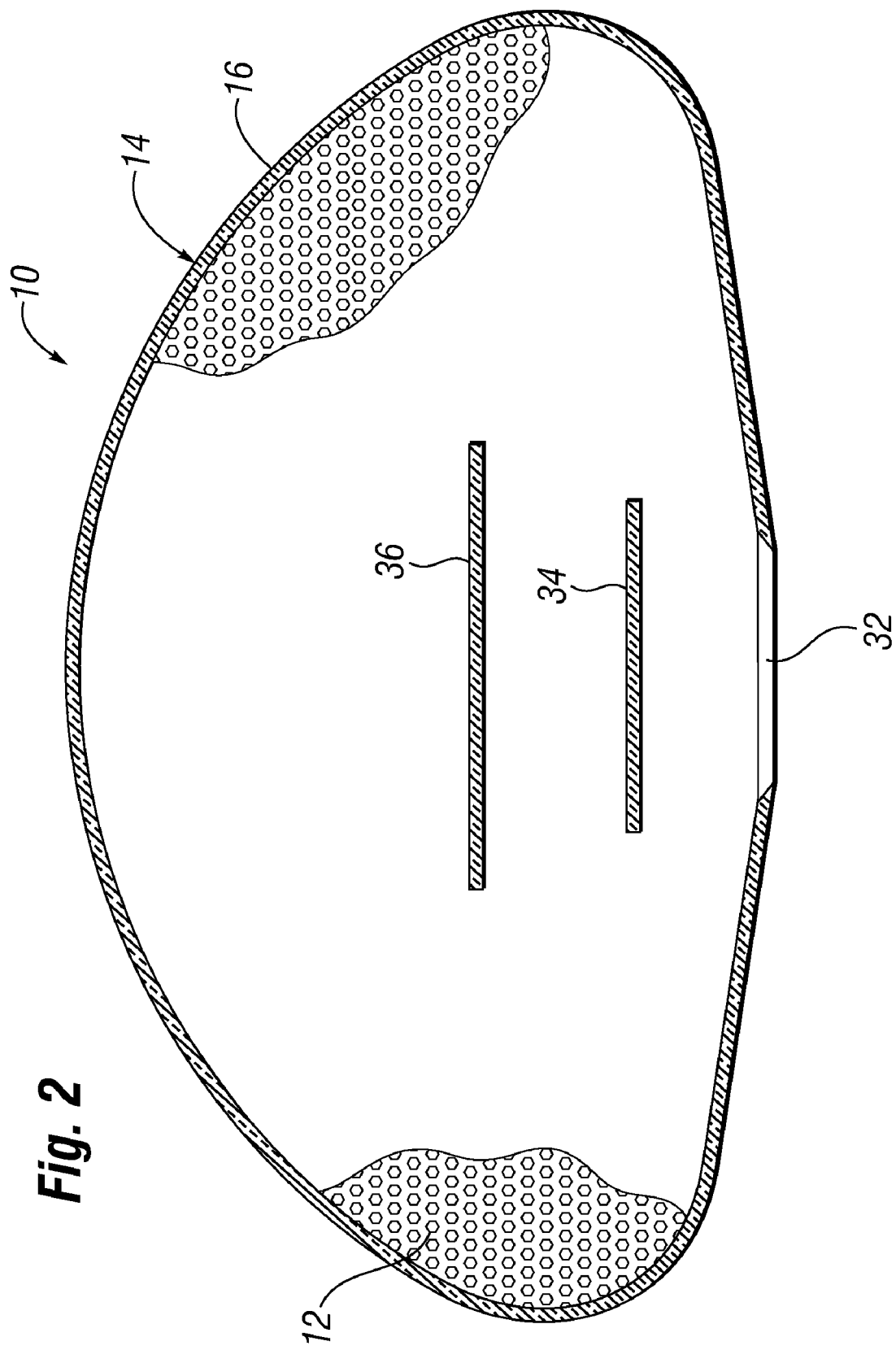

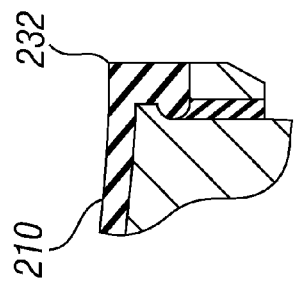
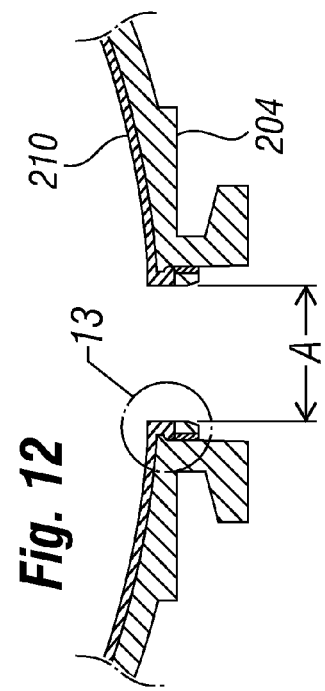
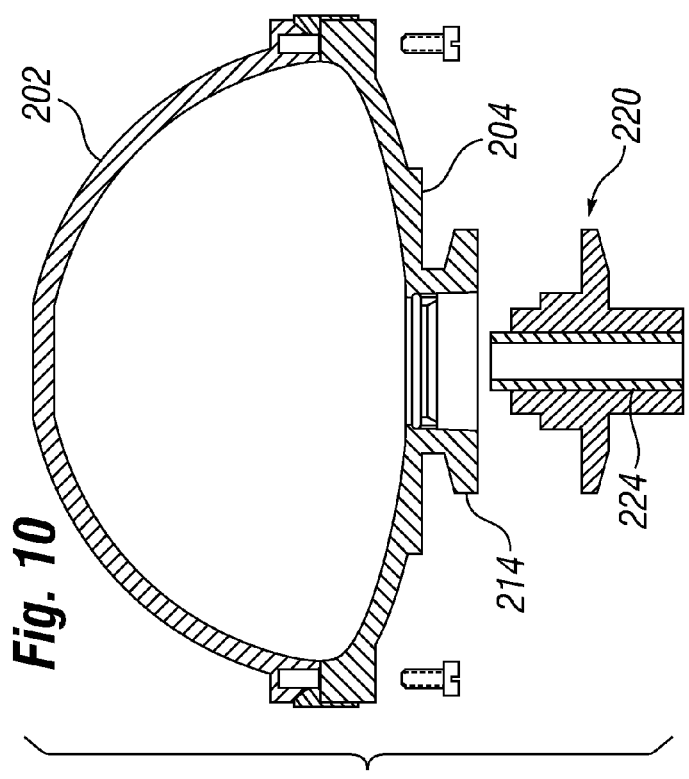
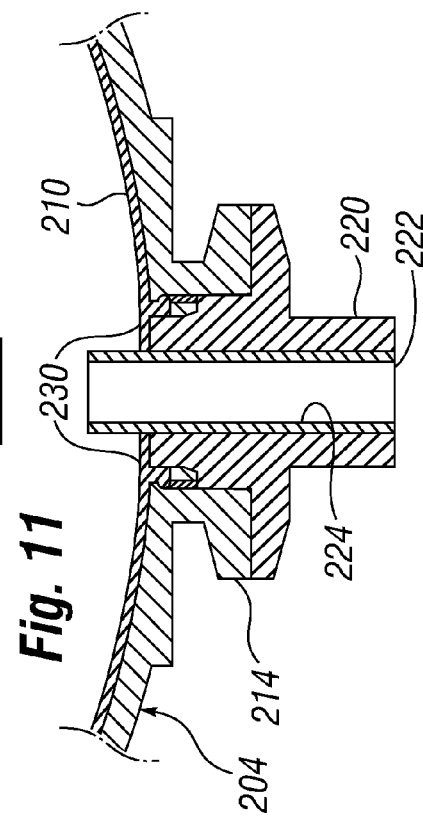

ALL-BARRIER ELASTOMERIC GEL-FILLED BREAST PROSTHESIS

RELATED APPLICATION

This application claims priority to U.S. Provisional Patent Application No. 60/952,304, filed on Jul. 27, 2007, the entire disclosure of which is incorporated herein by this reference.

FIELD OF THE INVENTION

The present invention relates to soft prosthetic implants and more specifically relates to silicone gel-filled breast implants and construction thereof.

BACKGROUND OF THE INVENTION

Implantable prostheses are commonly used to replace or augment body tissue. In the treatment of breast cancer, it is sometimes necessary to remove some or all of the mammary gland and surrounding tissue. Reconstruction of the breast commonly involves surgical implantation of a prosthesis which both supports surrounding tissue and restores the appearance of the breast. The restoration of the normal appearance of the body has an extremely beneficial psychological effect on post-operative patients, eliminating much of the shock and depression that often follows extensive surgical procedures. Implantable prostheses are also used more generally for restoring the normal appearance of soft tissue in various areas of the body, such as the buttocks, chin, calf, etc.

Soft implantable gel-filled prostheses typically include a flexible envelope or shell made of cured silicone-based elastomer encasing a silicone gel core. Obviously, a shell that is highly resistant to both rupture and the possibility of silicone gel bleeding through the shell is highly desirable. Breast implants have been designed with these goals in mind.

Conventional breast implant shells are multilayered or laminated. Specifically, such shells include outer "rupture-resistant" layers, and an inner "barrier" layer, sandwiched between the outer layers and effective to resist gel bleed. For example, some silicone-filled breast implants available from Allergan, Inc. include a low diffusion silicone elastomer shell made with outer layers of a dimethyl-diphenyl silicone elastomer, having a diphenyl polymer mole percent of 5%, and a barrier layer of dimethyl-diphenyl silicone elastomer having a diphenyl polymer mole percent of 15%.

Mentor Corp. manufactures gel-filled breast implants which include a layered silicone elastomer shell made with outer layers of a dimethyl silicone elastomer and an intermediate barrier layer of a dimethyl diphenyl silicone copolymer having a diphenyl polymer mole percentage of 15%.

One drawback of utilizing layered or laminated implant shells is that during formation of the shell, mixing of adjacent layers may result in visible clouding. Surgeons prefer a relatively transparent shell. Moreover, a shell having a layered construction presents the potential problem of delamination.

Despite many advances in the construction of soft prosthetic implant shells, there remains a need for a more flexible gel-filled prosthesis which minimizes gel bleed.

SUMMARY OF THE INVENTION

The present invention provides a gel-filled soft prosthetic implant, for example, a breast implant, comprising a silicone gel core and a flexible shell containing the core. In one aspect of the invention, the shell includes a layer of a silicone elastomer in direct contact with and enveloping the core such that the substantially homogenous layer is substantially saturated with said silicone gel. The present invention is based, at least in part, on the surprising discovery that the silicone elastomer layer of the shell has a wet strength, that is, a strength when saturated with said silicone gel, that is at least as great as its dry strength, that is, its strength in the absence of said gel.

More specifically, the shell is defined by a substantially homogenous layer of a silicone elastomer comprising a polysiloxane backbone and having a minimum mole percent of at least 10% of a substituted or pendant chemical group that sterically retards permeation of said silicone gel through the layer. More specifically, the silicone elastomer is a polydimethyl siloxane and the pendant chemical group is one of a phenyl group, for example, a diphenyl group or a methylphenyl group, a trifluoropropyl group, and mixtures thereof.

In an especially advantageous embodiment, the silicone elastomer comprises a polymer comprising dimethyl siloxane units interspersed with sufficient diphenyl siloxane units to provide said pendant chemical group that sterically retards permeation. In this embodiment, the mole percent of said diphenyl siloxane units is at least 13% and is no greater than about 25%. For example, the mole percentage of said diphenyl siloxane units is about 15%.

The shell may be substantially entirely defined by said substantially homogenous layer of said silicone elastomer. For example, in certain embodiments, the shell consists essentially of the single layer of the silicone elastomer material.

In yet other embodiments, the shell may further include at least one additional layer of another material located outwardly of the substantially homogenous layer, the at least one additional layer enveloping the substantially homogenous layer.

The shell preferably has a substantially uniform thickness of between about 0.1 mm to about 0.5 mm. For example, in the single layer embodiment, the shell has a substantially uniform thickness of about 0.3 mm.

Advantageously, the shell of the present implants has a bleed rate that is superior to, that is, less than, the bleed rate of a substantially similar shell having a conventional three layer structure when used in an identical manner and filled with an identical silicone gel. For example, when compared to a "layered" shell consisting of an intermediate silicone elastomer layer with 15% mole percent of the diphenyl group sandwiched between two outer silicone elastomer layers each with 5% mole percent of the diphenyl group, the single layer shells of the present implants have a significantly lower bleed rate. For example, in some embodiments, the bleed rate of the shells of the present implants is less than about 40% of the bleed rate of a shell constructed of a sandwich of an inner layer of 15% mole percent diphenyl between at least two layers of 5% mole percent diphenyl silicone elastomer.

In another aspect of the invention, methods of making silicone gel filled prosthetic implants are provided. For example, a method of preparing a silicone gel-filled implant in accordance with the invention generally comprises the steps of forming an envelope comprising a substantially homogenous layer of a silicone elastomer comprising a polysiloxane backbone and having a minimum mole percent of at least 10% of a pendant chemical group that sterically retards permeation of said silicone gel through the shell. The method further includes introducing a silicone gel precursor material into the shell such that the material is in direct contact with the shell inner surface, and curing the silicone gel precursor material to obtain a soft, silicone gel filled prosthetic implant.

In an especially advantageous embodiment, the silicone elastomer is a polydimethyl siloxane having a mole percent of about 15% of a diphenyl group. The step of introducing the silicone gel precursor material may be performed when the shell is in a dry or cured state. For example, once the shell has been formed, it may be placed in storage and removed later for filling with the silicone gel precursor material, and cured to form a silicone gel filled implant product.

Several systems and methods useful for forming, for example, casting, an elastomeric shell of an implant of the present invention are contemplated. In some embodiments, the step of forming the shell comprises coating a mandrel with a liquid silicone elastomer. For example, the shell may be formed by dipping a conventional, suitably shaped mandrel into a dispersion of a silicone elastomer and a solvent, allowing the solvent to evaporate, and allowing or causing the elastomer to cure or solidify while on the mandrel.

In other embodiments, the step of forming the shell comprises rotationally molding the shell, for example, using an uncured silicone elastomer material. In accordance with this embodiment, the casting process may include using a multi-axis rotational molding machine in which a suitably shaped mold is mounted. In operation, silicone elastomer or other suitable material is inserted into the mold while a vacuum is applied. The mold is rotated, for example, about at least two different axes, so that the silicone elastomer coats the inside walls of the mold and forms a single layer implant shell.

The present invention further provides a product made by the process comprising the steps of forming a silicone elastomer dispersion, coating a form with the dispersion; allowing solvent of the dispersion to evaporate to form a silicone elastomer film on the form, and removing the silicone elastomer film from the form. In addition, the process comprises saturating the silicone elastomer film with a silicone gel and curing the silicone gel saturating the silicone elastomer film to form a composite. Advantageously, in accordance with the invention, the composite has a comparable tensile strength to that of a substantially identical silicone elastomer film that is not saturated with silicone gel.

In yet another aspect of the invention, implants are provided wherein the implant comprises a silicone gel core and a shell enveloping the core that comprises a substantially homogenous layer of a silicone elastomer comprising a polysiloxane backbone and having a mole percent of at least about 10% of a pendant chemical group that sterically retards permeation of said silicone gel through the layer, and the substantially homogenous layer makes up at least about 20%, preferably about 50% or greater of the thickness of the shell. the substantially homogenous layer may make up at least about 90% of the thickness of the shell for example, as mentioned elsewhere herein, the shell may be substantially entirely defined by such substantially homogenous layer.

In a specific embodiment, the present implants are suitable for implantation in the human breast and the flexible shell is accordingly sized and shaped.

BRIEF DESCRIPTION OF THE DRAWINGS

Certain features, aspects and advantages of the present invention may be more clearly understood with reference to the following Detailed Description when considered in conjunction with the accompanying Drawings of which:

FIGS. 1A-1C show consecutive steps in a process of dip-forming a shell of a breast implant in accordance with some embodiments of the invention;

FIG. 2 is a cross-sectional, somewhat schematic view of a gel-filled breast implant in accordance with the invention;

FIGS. 8-13 illustrate components of a rotational molding system suitable for forming a shell of a breast implant of the present invention.

DETAILED DESCRIPTION

Figure 3:
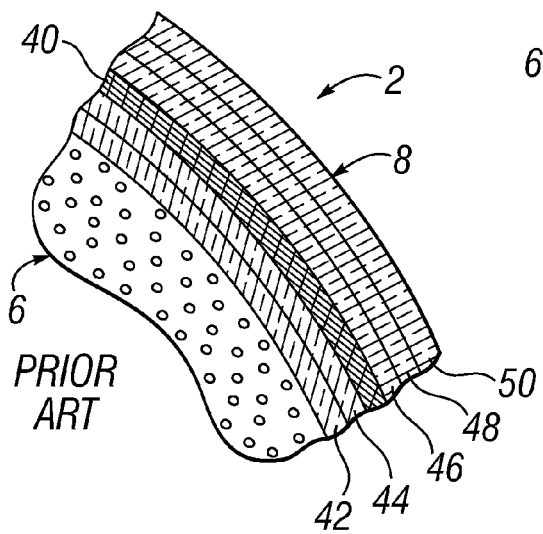
FIG. 3 is a cross-sectional view through a portion of a breast implant of the PRIOR ART.

The present invention provides a gel-filled implant, or prosthesis, constructed of an effective bleed resistant, rupture resistant shell surrounding and in direct contact with a silicone gel core.

In one aspect of the invention, the shell is defined by, for example, substantially entirely defined by, a single, substantially homogenous silicone elastomer layer. That is, the shells of many of the implants of the present invention are made of a single material of homogeneous or uniform composition, as opposed to a laminated or layered configuration common in conventional prosthetic implants.

The implants of the present invention may be suitable for use in reconstruction or augmenting the human breast. Other potential applications are implants for the buttocks, testes, calf, among other body areas, as well as tissue expanders therefor.

FIGS. 1A-1C illustrate, in somewhat simplified form, a suitable process for forming flexible implant shells for implantable prostheses, or implant, of the present invention.

Turning briefly to FIG. 2, in one aspect of the present invention a silicone gel implant 10, for example, a breast implant, is provided. The implant 10 comprises a silicone gel core 12 and a shell 14 comprising a substantially homogenous silicone elastomer layer 16 comprising a silicone elastomer polymer having a mole percent of at least 10%, for example, at least 13%, of a substituted chemical group that sterically retards permeation of the silicone gel through the shell 14.

Referring back to FIGS. 1A-1C, a suitable process generally involves coating a form, or mandrel 20 (FIG. 1A) with a silicone elastomer dispersion 22 (FIG. 1B). The dispersion 22 is a liquid, uncured elastomer material in a suitable solvent. When the silicone elastomer is a diphenyl dimethyl siloxane polymer, as in certain embodiments of the invention, the solvent may be any one or more of an aromatic or linear aliphatic of $C_6$ or greater, for example, xylene. The mandrel 20 is dipped into the dispersion 22 (FIG. 1B) and withdrawn therefrom. Excess silicone elastomer dispersion is allowed to drain from the coated mandrel 20a (FIG. 1C) and at least a portion of solvent of the dispersion is allowed to evaporate to stabilize the silicone elastomer coating on the mandrel.

The process may be repeated several times to form a coating of a desired thickness. Preferably, the solvent is allowed to evaporate after each coating. In the present invention, the coated mandrel is preferably repeatedly dipped into the same or an identical silicone elastomer dispersion, until a substantially homogenous elastomeric shell of a desired thickness is formed.

The silicone elastomer dispersion coating is cured on the mandrel using conventional means. For example, in some embodiments, the coating 20a is heat cured. Curing may be accelerated by the use of circulating air or other known means. The cured material is soft, flexible and elastic.

After the silicone elastomer coating has been cured on the mandrel, the cured material is removed from the mandrel by stretching the hole in the coating at the mandrel attachment site. Once removed from the mandrel, the coating is in the form of a hollow, substantially homogenous, silicone elastomer envelope which, when filled with uncured silicone gel, will make up at least 20%, more preferably, at least 30%, more preferably, at least 50% or greater in terms of average thickness of the shell 14 of the implant 10 shown in FIG. 2. in some embodiments, the substantially homogenous, silicone elastomer envelope makes up substantially the entire thickness of the shell 14.

Before the shell 14 is filled with silicone gel precursor material, the hole 32 on the shell 14 (formed at the mandrel attachment site) is sealed, for example, by attaching an uncured silicone elastomer portion 34 and a cured silicone elastomer portion 36 to a periphery of the hole 32. After sealing the shell 14, an uncured or precursor silicone gel material which will form the core 12 is introduced, for example, injected, into the shell 14, for example, with the aid of a needle inserted through the patch site 34, 36. The silicone gel precursor may be supplied as a two-part liquid system with a primary gel component and a cross-linking component. The needle entrance may be sealed using suitable means, for example by applying an adhesive thereto. Such silicone gel precursor materials and their uses in the manufacture of breast implants are well known in the art and will therefore not be described in greater detail herein.

In addition, processes of forming a breast prosthesis including dipping a mandrel into a silicone elastomer dispersion to form an implant shell, patching the hole in the shell and filling the shell, are well known in the art and will not be described in great detail herein. Murphy, U.S. Pat. No. 6,074,421, the entire disclosure of which is incorporated herein, describes advantageous methods of patching a hole in a shell of a breast prosthesis. Many of the manufacturing steps described in Murphy, particularly those steps involving patching a shell hole to form a seamless implant shell, can be used in the manufacture of the present implants.

As shown in FIG. 2, silicone gel material making up the core 12 is in direct contact with the silicone elastomer shell 14. As will be described in greater detail elsewhere herein, the silicone elastomer shell 14 may be defined by a single, substantially homogenous layer of elastomeric polymer having a polysiloxane backbone and having a minimum mole percent of about 10% of a pendant chemical group that sterically retards permeation of said silicone gel through the substantially homogenous layer 16. During formation of the implant, the silicone gel saturates, or substantially saturates the inner surface of the substantially homogenous layer 16. The polymeric material making up layer 16, absent such saturation with silicone gel, may be substantially equivalent or identical to the polymeric material which forms a conventional intermediate, or so called "barrier layer", of a multilayered implant shell of the prior art.

FIG. 3 illustrates, in cross-section, a portion of a PRIOR ART breast implant 2 including a silicone gel core 6 and a smooth-walled, multilayered shell 8. The primary barrier to silicone gel bleed through the shell wall 8 is provided by an inner so called "barrier layer" 40. In this example, of the PRIOR ART, two base coat layers 42, 44 lie radially inward from the barrier layer 40, with one of said base coat layers 42 being in direct contact with and substantially saturated with the silicone gel material making up the core 6. In this example, three further base coat layers 46, 48, 50 are provided on the outer side of the barrier layer 40 as shown. Typically, the base coat layers 42-50, including the layer in direct contact with the gel core 6, are a dimethyl silicone copolymer with no diphenyl substituted groups, or a dimethyl-diphenyl silicone copolymer including a small percentage of diphenyl polymer substituted groups (e.g., mole percent of 5%). The base coat layers 42-50 are designed to be rupture resistant. Unlike the base coat layers 42-50, the intermediate barrier layer 40 is a dimethyl diphenyl silicone copolymer having a relatively higher percentage of a diphenyl polymer component (mole percent of 15%), as is designed to reduce gel bleed through the shell 8.

The multilayered shell 8 of the PRIOR ART implant has an average thickness of about 0.5 mm. The thickness of the barrier layer 40 is typically no greater than about 10% of the total shell wall thickness, or between about 0.025-0.050 mm. In such PRIOR ART implant shells, the barrier layer 40 is limited to a relatively minor proportion of the overall wall thickness of the shell. This is based on the conventional wisdom that this polymer is a generally relatively weak elastomer, for example, in terms of tensile strength, and is only included as an "intermediate layer" for promoting bleed resistance. It is also conventionally believed that these silicone elastomers, including those that make up the so called barrier layer materials, decrease in tensile strength when saturated with silicone gel, the thin barrier layer 40 is also conventionally "sandwiched" between the base coat layers, and is not placed in direct contact with the silicone gel filling making up the core 6.

Figure 4:
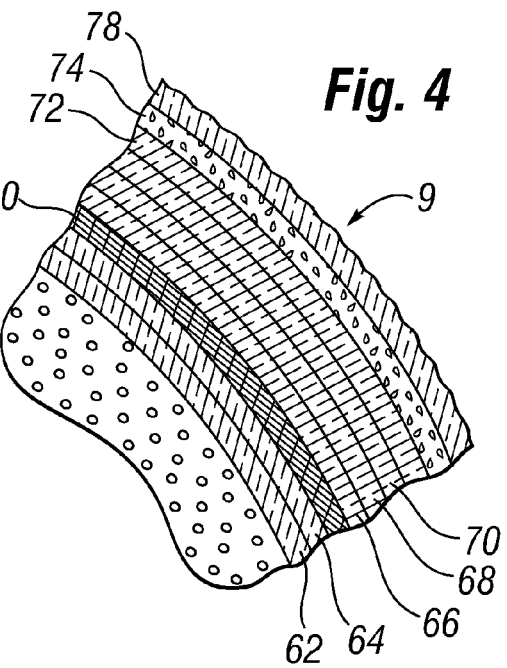
FIG. 4 is a cross-sectional view through a portion of another breast implant of the PRIOR ART.

FIG. 4 illustrates in cross-section a layered portion of a textured implant 9 of the PRIOR ART. Like the PRIOR ART implant 2 shown in FIG. 3, the primary barrier to gel bleed through the shell wall is provided by an inner barrier layer 60. Two so-called base coat layers 62, 64 lie radially inward from the barrier layer 60. On the outer side of the barrier layer 60, three further base coat layers 66, 68, 70 are provided. Furthermore, outside of the outer base coat layers 60-70, a tack coat layer 72, a layer of textured crystals 74, and an overcoat layer 78 are provided. As with the smooth-walled PRIOR ART implant of FIG. 3, the base coat layers 62-70 are a dimethyl silicone copolymer or a dimethyl-diphenyl silicone copolymer with a small mole percentage of diphenyl component (e.g., 5%), and the barrier layer 60 is a dimethyl-diphenyl silicone copolymer having a higher mole percentage of diphenyl polymer (e.g. 15%).

It is well known that the strength, for example, tensile strength, of shells of polydiphenyl siloxane material in the prior art decreases once contacted with or saturated with silicone gel. A surprising discovery made during development of the present invention is that the material typically used as an intermediate layer, or barrier layer, (for example, layer 40 shown in FIG. 3, and layer 60 shown in FIG. 4) in conventional multilayered implant shells has a comparable tensile strength or perhaps even a higher tensile strength when the barrier layer material is placed in direct contact with, or is substantially saturated with, the silicone gel during filling of the implant and is in direct contact with the silicone gel in the finished implant product.

Whereas in prior art implants in which so-called barrier layer materials having a relatively higher mold percentage (i.e. greater than 10%) of pendant diphenyl groups are separated from and not in direct contact with the silicone gel core, for example, are "sandwiched" between base coat layers having a relatively lower mole percent of diphenyl groups, many of the implants of the present invention comprise such barrier layer materials which envelope and are in direct contact with the silicone gel core.

Furthermore, whereas in prior art implants in which so-called barrier layer materials having a relatively higher mold percentage (i.e. greater than 10%) of pendant diphenyl groups are minimized in terms of the amount of such materials making up the shell of the implant, many of the implants of the present invention include such barrier layer materials which make up of a significant percentage, in terms of thickness, of the implant shell.

For example, in accordance with some embodiments of the present invention, the shell may comprise a substantially homogenous layer having a mole percentage of at least about 10% of diphenyl siloxane units which said substantially homogenous layer makes up at least about 20%, or at least about 30%, or at least about 50% or more of the thickness of the shell. In some embodiments of the invention, said substantially homogenous layer makes up between about 50% and about 90% of the average thickness of the shell. In some embodiments, said substantially homogenous layer makes up the substantial entire thickness of the shell.

Figure 5:
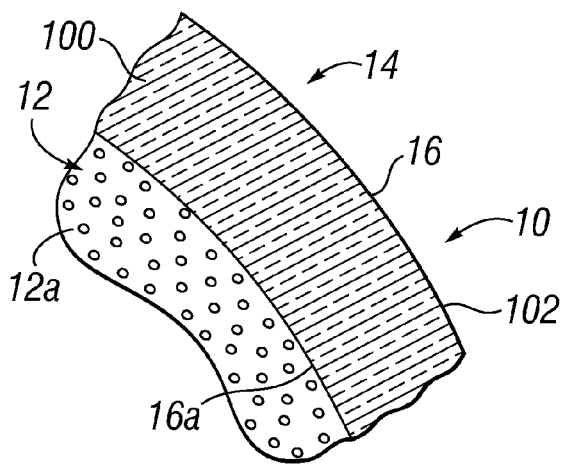
FIG. 5 is a cross-sectional view through a portion of an implant of the present invention having a single layer shell.

More particularly, FIG. 5 illustrates a close up view, in cross-section, of a portion of the exemplary implant 10 of the present invention shown in FIG. 2. In this embodiment, the shell 14 comprises a single, substantially uniform barrier layer 16 comprising a homogeneous silicone elastomer having a minimum mole percent of at least 10%, and more preferably, about 13%, for example, about 15%, of a substituted chemical group that sterically retards permeation of the silicone gel through the shell 14. In some embodiments the shell 14 is substantially entirely defined by the single barrier layer 16. Layer 16 includes an inner surface 16a which is in direct contact with, and is substantially saturated with the gel material 12a which makes up the core 12.

Figure 5A:
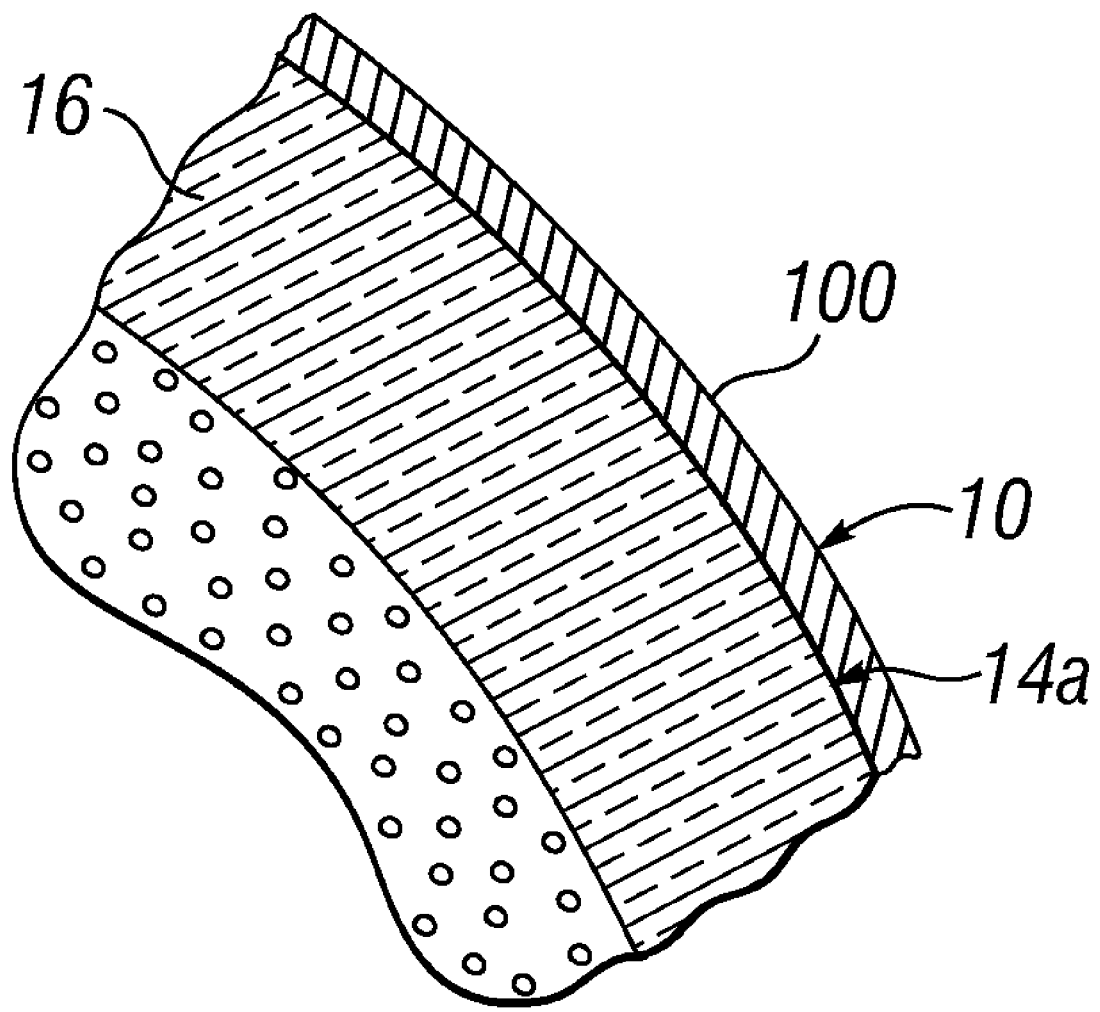
FIG. 5A a cross-sectional view of a portion of another implant of the present invention having a multilayered shell.

Turning now to FIG. 5A a cross sectional view of a portion of another implant 10a in accordance with the invention is shown. Implant 10a may be identical to implant 10, except that rather than comprising a shell 14 substantially entirely comprising or consisting of a single substantially homogenous layer 16, shell 14a of implant 10a includes at least one additional layer 100 overlying and enveloping said substantially homogenous layer 16. Additional layer 100 may comprise a dimethyl silicone copolymer with no diphenyl substituted groups, or a dimethyl-diphenyl silicone copolymer including a relatively small percentage of diphenyl polymer substituted groups (e.g., mole percent of less than 10%, for example, about 5%).

Figure 6:
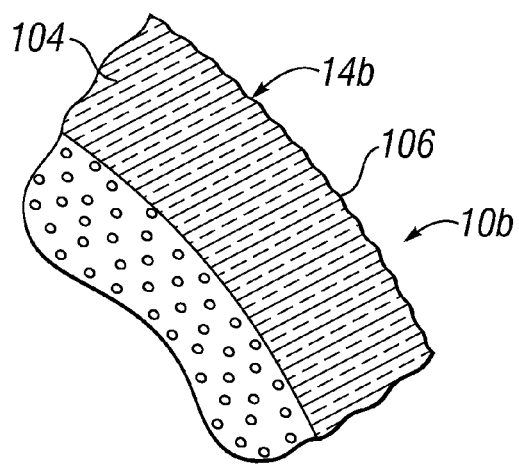
FIG. 6 is a cross-sectional view through a portion of an implant of the present invention having a single layer, textured shell.

Turning back to FIG. 5, the outer surface 102 of the shell 14 may be smooth, as in conventional smooth-walled implants. Alternatively, as shown in FIG. 6, an implant 10b in accordance with another embodiment of the invention may comprise a shell 14b having a textured outer surface 106, wherein implant 10 and implant 10b may be substantially identical to one another with the exception of the texturing of the shell 14a. Such texturing can be formed by a variety of processes including texturing on the mold used to form the outer surface 106 of the shell 14a.

For purpose of definition, siloxane is defined as any of various compounds based on a polysiloxane backbone of alternating silica and oxygen molecules. When the side chain substituents or pendants are organic radicals, they are silicones. Polydimethyl siloxane consists of a siloxane with two methyl ($CH_3$) substituted groups, and polydiphenyl siloxane consists of a siloxane with two phenyl ($C_6H_5$) substituted groups.

It is important to clearly define the exemplary and preferred materials that may be used for the "all-barrier" shells, such as shell 14, of the implants of the present invention. First, the materials are polysiloxanes, or silicone polymers. These materials are commercially available from suppliers such as NuSil Technology based in Carpenteria, Calif. The basic formula of medical grade polysiloxanes is a polydimethylsiloxane (silicone elastomer chain) with or without other radical groups substituted for the methyl groups. The following formula is a polydimethylsiloxane or dimethyl silicone elastomer, which is currently used as the outer layers in the Mentor MemoryGel™ implants:

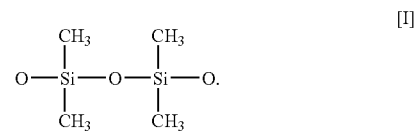

[I]

The following formula is the polydimethylsiloxane above with a methyl-phenyl substituted group:

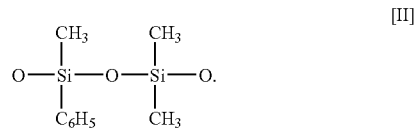

[II]

The steric hindrance of the large phenyl group significantly prohibits high concentrations of diphenyl units on the polymer chain. Steric hindrance or steric resistance occurs when the size of groups within a molecule prevents chemical reactions that are observed in related smaller molecules. In general, a molecule that sterically hinders other molecules generally hinders their free movement. Steric hindrance between adjacent groups can also restrict torsional bond angles.

Finally, formula III below is a polydimethyl siloxane above with a diphenyl substituted group:

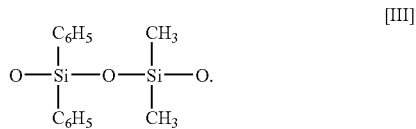

[III]

Again, the steric hindrance of the large phenyl groups often limits their concentration in the polymer to a maximum mole percent. It is believed that maximum mole percent for the diphenyl substituted group is about 25% before the steric interference of the large phenyl groups starts to make the compound unstable. This instability makes manufacture of the polymer difficult if not impossible.

Other pendant groups that are well known in the art may be present in the polymer at a mole percent greater than 25%. For example, some pendant groups, for example, the flouro groups may be present in a mole percent of nearly up to 100% of the substituted chemical groups without loss of stability of the polymer. Such polymers may be useful as components of the shells of the implants of the present invention, and are considered to be included within the scope of the invention.

One key aim of designers of materials for prosthetic implant shells is to reduce the amount of bleeding of the filler gels through the shell. The filler gels in soft prosthetic implants are 10-20% crosslinked silicone including silicone oils. The compatibility of the silicone gel and surrounding silicone elastomer shell causes some of the silicone oil to absorb into and swell the shell. Such swelling lowers shell tensile strength. However, although some bleeding of the gel through the shell occurs, once the shell is saturated or swelled the presence of silicone on the outside of the shell reduces the tendency of the gel to further bleed through the shell. This is a result of the reduced chemical gradient across the shell and thus reduced osmotic pressure that leads to bleeding.

After gel saturation, some bleeding still occurs, and it is desirable to minimize it. Although silicone-based shells tend to bleed at least a small amount, the material properties of softness or suppleness make them practically the only material choice. Some studies are ongoing as to polyurethane or polyurethane-silicone copolymer shells, though as yet these have yet to be commercially adopted. It is feasible that a suitable material other than silicone will one day be available, in which case the concept of a single layer barrier shell may apply thereto, however the present invention is concerned with silicone elastomers.

Although not wishing to be bound by any particular theory of operation of the present invention, it is believed that in addition to limiting the proportion of the substituted groups, the large phenyl groups sterically retard permeation or bleeding of the silicone gel through the shell. This occurs because the larger phenyl groups physically restrict the free movement of the gel filler throughout the shell. This reduces solubility of gel in the shell and lowers the saturation point which, consequently, helps maintain the physical properties, such as strength, of the shell, relative to shells or layers made of silicone elastomers having a lower percentage of such substituted groups or those that are absent of such substituted groups.

The extent of saturation and bleeding may be based on the solubility of the gel in the silicone elastomer. For example, a mole percent of about 15% of the substituted phenyl groups allows a lower degree of saturation because the higher, or more preferably about 13% or In accordance with the present invention, the minimum mole percent of the substituted diphenyl group that sterically retards permeation of the silicone gel through the shell is at least about 10%, for example, about 13%. In a preferred embodiment of the invention, the preferred material for the barrier layers 16 forming at least a portion of the shell 12 is a substantially homogeneous layer, for example, a single, substantially homogenous layer, of dimethyl polysiloxane having a minimum mole percent of about 15% of a pendant or substituted diphenyl group (see Formula III. above). Therefore, the preferred material for the shells of the present implants is a dimethyl polysiloxane having a mole percent of between about 10%, and more preferably, between about 13% and about 25% of a substituted diphenyl group.

The efficacy of substituted diphenyl groups is known, though other a substituted groups may also work. For instance, the substituted group may be a fluoro group. Formula IV. below is a polydimethylsiloxane above with a trifluoropropyl substituted group:

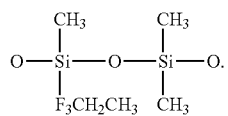

[IV]

The minimum mole percent of the substituted fluoro group that sterically retards permeation of the silicone gel through the shell will be different than that for the diphenyl substituted group. The materials described herein may be empirically tested to determine their capacity for sterically retarding silicone gel permeation. One method is to test the materials to see how much swelling occurs upon contact with silicone gel on one side. Such testing can be performed on sheets of the material. Though not wishing to be bound by any particular theory of operation, it is believed that the greater the amount of swelling of the material, the lesser the capacity of the material for retardation of gel permeation.

Alternatively, cast shells may be formed and filled with gel after which a gel bleed test is conducted. A bleed test essentially measures the amount of gel that passes through the implant shell over a period of time. Testing is done according to ASTM standard F703, and the bleed results are typically given the units mass/surface area/time, e.g., $\mu g/cm^2$/days. In the context of the present invention, the following table quantifies the bleed rate of the number of materials discussed herein relative to the bleed rate for a dimethyl silicone elastomer, which will be arbitrarily assigned a value of 100. Note that the percent units in the shell material column refer to the mole percent.

| Shell material | Bleed rate |
| --- | --- |
| All dimethyl silicone elastomer | 100 |
| All 5% diphenyl silicone elastomer | 95 |
| Sandwich of 15% diphenyl between 5% diphenyl silicone elastomer | 15-20 |
| All 15% diphenyl silicone elastomer | 5-10 |

In comparison to the sandwich of 15% diphenyl between 5% diphenyl silicone elastomer, which is currently used in implant shells manufactured by Allergan, the present invention of a shell made entirely of a 15% diphenyl silicone elastomer has a bleed rate that is approximately 40% less. Moreover, the homogeneous nature of the single layer shell eliminates the possibility of both clouding and delamination which may occur with layered shells.

In addition to the ability to retard gel bleeding, suitable implant shells must also possess a minimum strength to resist rupture. Indeed, the primary design criteria for implant shells have been and continue to be the ability to resist rupture. That was the reason for using a layered approach in the past, with presumably stronger materials coupled with the inner, weaker barrier layer. The standard methodology of measuring the strength of silicone materials such as used in the shells of the present invention is the well-known ASTM tensile strength test utilizing a dog-bone sample. Samples are either manufactured in the requisite shape, or are cut from a formed implant shell. The ends of the sample are uni-axially pulled in opposite directions until the sample fails. Although the single layer shells of the present invention are weaker than previous layered shells when dry, they have a comparable strength, perhaps a greater strength, when wet or saturated with gel. That is, after an implant shell is filled with the silicone gel, it swells and becomes saturated. The strength of silicone shells typically decreases after swelling. However, the reduction in strength is less or insignificant for shells of the present invention perhaps due to the reduced swelling with gel relative to conventional layer materials and earlier shell constructions.

The following table illustrates this phenomena.

| | Shell Construction | Average Tensile Strength (psi) n = 15 | | |
|---|---|---|---|---|
| | | Dry (no gel contact) | Wet (from finished gel-filled device) | % Change in Strength |
| A | All 5% diphenyl silicone elastomer | 2202 | 1408 | −30% |
| B | Sandwich of 15% diphenyl between 5% diphenyl silicone elastomer | 1920 | 1582 | −18% |
| C | All 15% diphenyl silicone elastomer | 1541 | 1641 | +6% |

From these tests an earlier material with no barrier layer (A) and the current layered material (B) demonstrate a reduction of 30% and 18%, respectively, in strength after exposure to silicone gel (i.e., wet strength). However, the all-barrier material C actually has a comparable or increased wet strength relative to its dry strength. Indeed, the resulting strength of the all barrier material C after exposure to silicone gel is greater in absolute terms than the wet strength of the materials A and B. Desirably, shells of some implants of the present invention are constructed of a substantially homogeneous barrier material in a single layer whose wet strength is comparable to or greater than the wet strength of conventional layered materials.

The wall thickness of the substantially homogenous layer 16 is preferably between about 0.1 mm and about 0.5 mm, for example, at least about 0.3 mm. It should be noted that the thickness at any one point around the shell 14 may be greater or less because of casting imprecision. For example, in some embodiments, the thickness of the substantially homogenous layer 16 ranges from about 0.3 mm to about 1 mm.

Furthermore, with the textured shell layer 14b of FIG. 6, the thickness varies due to the peaks and valleys of the rough surface 106. The textured outer surface 106 may be formed by texturing the casting surface, or other suitable means. The textured shell 14b of the implant 10b shown in FIG. 6, which may be substantially entirely defined by single substantially homogenous layer 14b, can be made much thinner than conventional layered textured shells, resulting in an extremely supple textured implant, relative to prior art layered textured implants.

The Young's Modulus (E) of the shells 14 and 14b made with the single layer construction may be less than the prior art shells of a sandwiched or layered construction. In one embodiment, the single homogeneous layer 14, 14b is formed exclusively of dimethyl polysiloxane having a minimum mole percent of about 15% of a substituted diphenyl group, and the Young's Modulus of such a material is less than that of a dimethyl-diphenyl silicone copolymer with a mole percent of 5% of a diphenyl component, which is what is used in the layered shells of FIGS. 3 and 4.

Although the shells 14, 14a and 14b in accordance with the present invention can be formed in a number of ways, including the dipping method described above with respect to FIGS. 1A-1C, a preferred system and method is disclosed in U.S. Pat. No. 6,602,452 to Schuessler, which is expressly incorporated herein by reference. Schuessler discloses a rotational molding machine for forming medical articles, in particular for molding silicone elastomer shells for breast implants.

Figure 7:
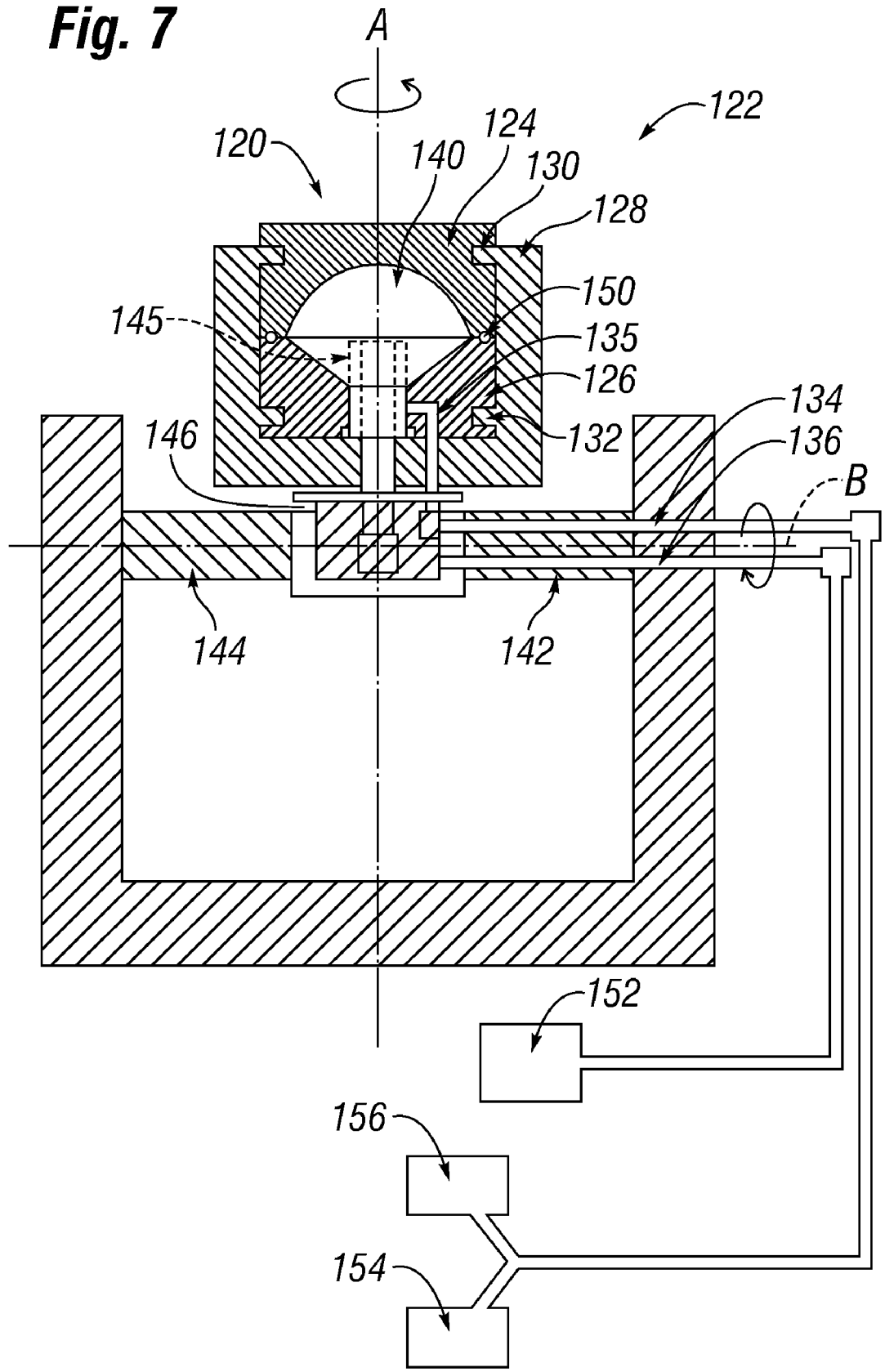
FIG. 7 is a schematic cross-section of an exemplary rotational molding system suitable for forming a shell of a breast implant of the present invention.
Figure 8:
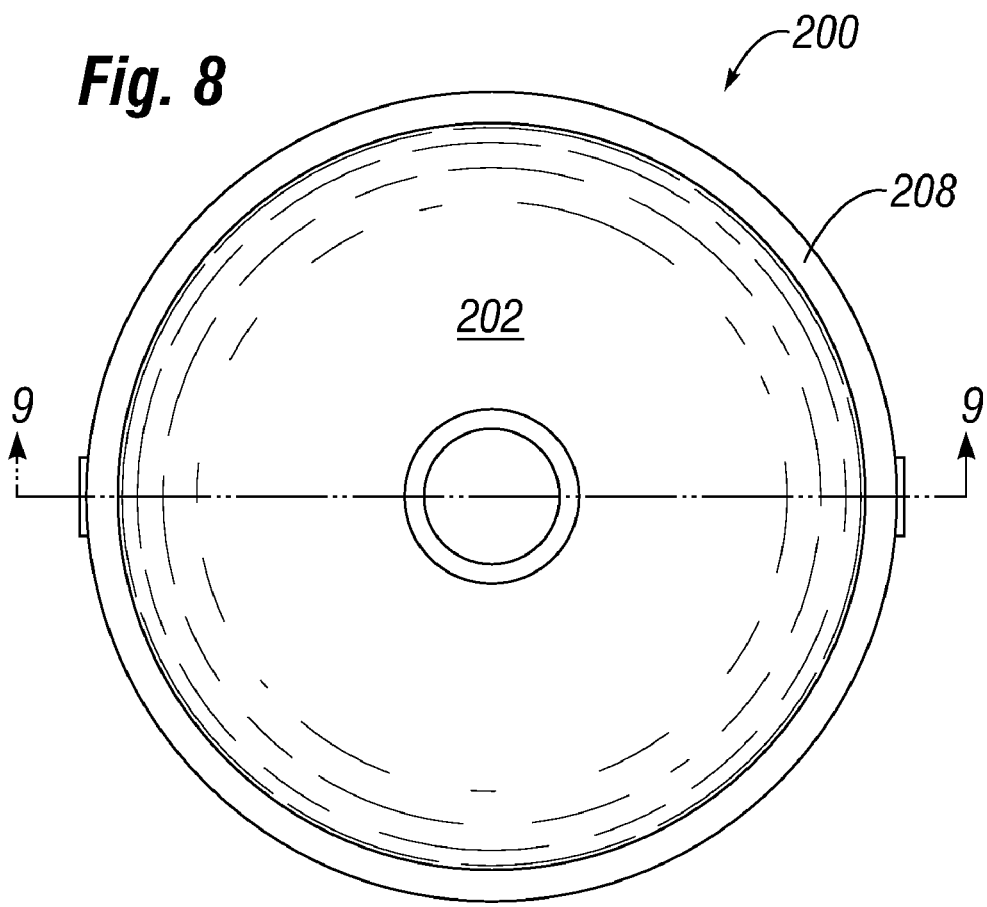
Figure 9:
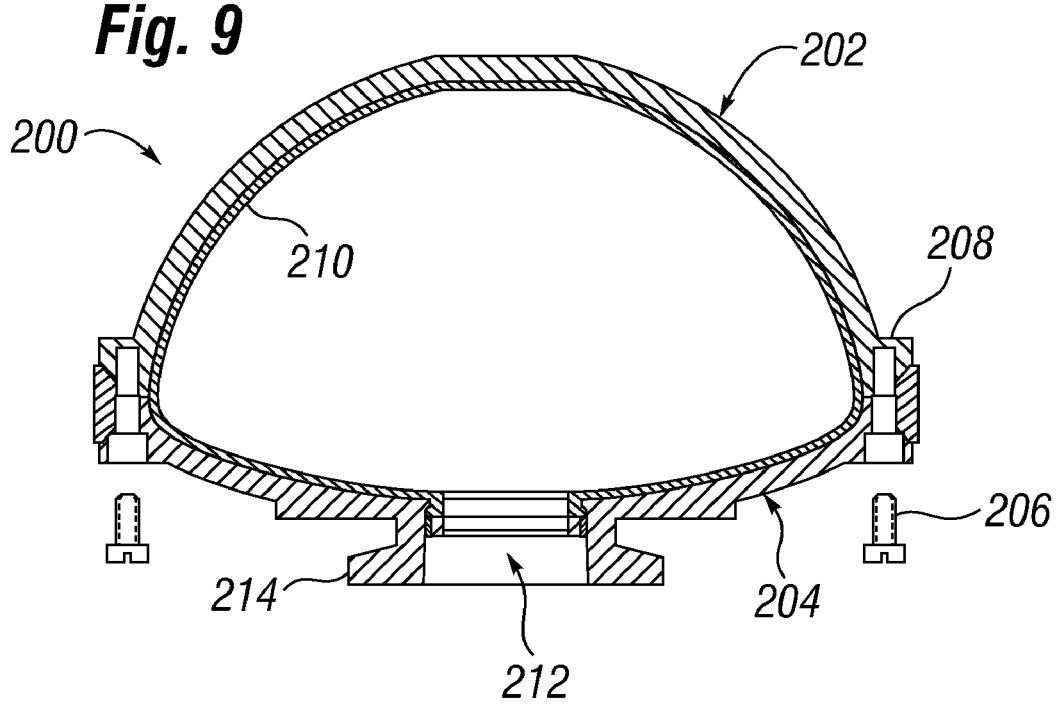

FIG. 7 is a schematic of an embodiment of a rotational molding system similar to that disclosed in Schuessler, which can be used to form implant shells of the present invention. A two-piece case mold 120 is fixed to a multi-axis rotational mold machine 122 by clamps securing top mold piece 124 and bottom mold piece 126 to clamp base 128 at top locking groove 130 and bottom locking groove 132 respectively. Vacuum connection 134 runs through one arm of the mold machine 122 to the vacuum opening 135. Additionally, material connection tube 136, through which silicone elastomer, liner materials, and/or air are injected into the mold cavity 140, may run through or along the same arm 142 as the vacuum connection 134 or by means of another arm 144. Fluid then continues through a circular sprue tube 145 fitted in a circular opening (not numbered) of bottom mold piece 122. The sprue tube 145 defines a hollow bore that allows materials to enter into the two-piece case mold 120 when the bottom mold piece 122 and the top mold piece 124 mate.

The hub 146 of the two arms rotates about axis A in the horizontal direction, while the arms 142, 144 rotate about axis B, which may be perpendicular to axis A. This allows the liner material and silicone elastomer material to uniformly coat the surface of the mold cavity 140. Two-piece case mold 120 may be manufactured from copper, aluminum, or other materials. The top mold piece 124 and bottom mold piece 126 are fitted together at their mating surfaces, sealed with O-ring 150, and then locked into clamp base 128 of multi-axis rotational molding machine 122.

Material reservoir 152 is fluidly coupled to connection tube 136 for providing silicone elastomer, liner material and/or air to cavity 140. Vacuum source 154 and solvent condenser 156 are fluidly coupled to vacuum connection 134. The hollow bore of the sprue tube 145 communicates with an inner vacuum tube (not shown) which in turn is connected to vacuum opening 135 and vacuum connection 134.

The rotational molding system of FIG. 7 has at least two distinct advantages over earlier methods for forming soft implant shells.

First, rotational molding of silicones and other solvent-based or gas-emitting materials has not previously been feasible because silicone elastomers with the necessary physical properties for use with medical devices are usually high in molecular weight or require fillers. These materials typically have too high of a viscosity and need to be combined with a solvent to make a dispersion having a suitable viscosity. This solvent-based, reduced viscosity dispersion allows application of the silicone polymer onto a mandrel by spraying or dipping after which the solvent is allowed to evaporate. However solvent-based dispersions have not been practical for use in a rotational molding process since there is no ready means to remove the significant volume of solvent vapors that are trapped within the closed molds. The system of FIG. 7 includes a vacuum vent to the mold via a rotating arm of the equipment, which removes the solvent while the arm is rotating and the dispersion material is flowing and being deposited on the inner surface of the mold.

A second advantage of the rotational molding system is that is enables the formation of seamless articles. The mold parting lines that would otherwise be formed at intersection of the mold halves are eliminated in the process of the present invention by first coating the inside of the assembled, multi-part mold with a thin layer of molding material such as polyethylene, polypropylene, nylon, fluoropolymer, polyester resin, polyurethane, epoxy or the like to create a mold liner. After the liner is cast, then the raw material, e.g. silicone elastomer, for the desired implant shell is injected into the mold cavity and similarly rotationally cast inside the liner, resulting in a temporary laminated construct. When the mold is disassembled and the construct is removed from the mold, the liner material and the implant are physically separated resulting in the desired article having a seamless configuration.

The first step in manufacturing an implant shell utilizing the multi-axis rotational molding system of FIG. 7 is to make a liner which coats the internal mold surface of the two-piece case mold 120. The liner should cover the interior domed surfaces of top and the bottom mold halves 124, 126. Covering the internal mold surfaces thus masks any interruptions in the surface, such as the mold parting lines, machining marks located on the internal mold surface, or minor damage to the internal mold surface.

The liner may be any suitable material but should meet several requirements. First, the liner should have a low extractability level so it is biocompatible with the implant shell or other molded article. The liner should also be resistant to any solvent or solvents being used in the silicone elastomer used in making the implant shell or other molded article. The liner material should be able to completely and uniformly coat the internal mold surface during the rotation of the mold by the multi-axis rotational molding machine. If heat is used to cure the silicone elastomer during the molding process, the liner should have a high level of heat resistance. The liner should be easily removable or releaseable from the mold surface and from the cured shell. Lastly, the liner may be used to impart a desired surface finish to the silicone elastomer, e.g. glossy, matte, textured, etc. Suitable liner materials include: polyethylene (Equistar™ #MP658-662), polypropylene (A. Schulman™ #PD 8020), nylon (Capron® #8280); fluoropolymers (DuPont® Teflon® PFA), polyester resin (Hypol™ #320300-10), polyurethane (Smooth-On Smooth Cast #305) and epoxy (Polytek® Development Corp. Polypoxy® 1010), all of which can be found on the open market. A skilled artisan in the field will recognize that other similar materials can replace these listed liner materials.

A predetermined volume or weight of the chosen liner material is dispensed into the mold so as to produce a lining of the desired thickness. The liner material is either in the form of a fine powder or a liquid depending on the selection of the liner material as long as the selected material is free flowing. The liner material is inserted into the two-piece case mold 120 through circular sprue tube 145. The sprue tube 145 extends approximately halfway into the interior cavity 140 of case mold 120 and remains in this position during the entire process of forming a liner and shell or other article. The liner material can be inserted into the case mold prior to the case mold being locked into the rotational arms of the multi-axis rotational molding machine or after the case mold has been locked into the rotational arms. The closed mold 120 is rotated about two or more axes allowing the liner material inside to form a consistent coating along the internal surface of cavity 140. The rotation of the mold about the axes forms a liner of uniform thickness. If the liner material is composed of thermoplastics, heat is applied so as to cause the liner material to melt and coat the inside mold surface as per conventional rotational molding techniques. In the case a chemical set is used for the liner material system, such as a polyester resin, no heat needs to be applied. In addition, air pressure, vacuum, inert gas such as nitrogen or other vapors or solid particles may be applied to the interior of the mold to minimize bubbles or to affect the surface finish of the liner in the desired manner.

Once the liner has been formed, the next step is to form the implant shell. Circular sprue tube 145 remains extending into the mold cavity 140 during the entire process of curing the liner and the molding material. To keep the sprue tube 145 clean and to maintain a vacuum during the casting step, the exterior end of the sprue has a removable cap. Silicone elastomer is injected into the interior of the mold. A predetermined amount of molding material is inserted based on the desired size and thickness of the finished shell or article. The desired polysiloxanes with substituted groups to retard gel bleeding used to form the single layer implants are described above.

After the silicone elastomer has been dispensed into the mold cavity 140 with the liner via the sprue tube 145, the mold is rotated around at least two axes while a vacuum is applied to its interior. The vacuum may be applied in different fashions. The vacuum can be applied to the sprue of a sealed mold by way of the vacuum opening 135. The vacuum may also be applied to the interior cavity or chamber in which an open sprue mold is rotating. Alternatively, the mold may be constructed of a porous material and a vacuum applied to the exterior of such porous mold. In addition, positive pressure using either, or in combination, air, nitrogen, or other gases may be applied intermittently to aid in bubble removal within the silicone elastomer. Bubbles need to be removed to allow for a uniform smooth surface of the liner, and ultimately the shell or other molded article.

The silicone elastomer is rotated and allowed to cure as the arms of the rotational molding machine rotate around their axes, thereby forming the desired shape. Rotating the mold at different speeds can compensate for different viscosities of the inserted materials. Heat is applied if necessary or to accelerate the curing process. The silicone elastomer sets up and stops flowing as it is rotated and cures in place on the liner material. If additional wall thickness is desired for the shell or other molded article, the steps may also repeated, though the finished product should be a single homogenous materials or layer. That is, the rotational molding process (and indeed the dip process described previously) may be done in multiple stages or steps, each step adding more material. However, the finished product exhibits no distinct layers and the entire shell wall is homogenous or uniform in composition.

After the cure cycle has been completed and the silicone elastomer has been cured to the desired thickness the formed shell or article surrounded by the liner is removed from the mold. The shell or other molded article is separated from the liner by one of the following methods appropriate to the liner system: dissolving the liner in a suitable solvent; melting or burning the liner away from the more temperature resistant shell or molded article; tearing or breaking the liner away from the shell; or peeling the flexible formed shell away from the liner and removing it through the opening in the liner created by the sprue opening. The liner may be discarded, or if the liner has not been damaged or dissolved depending on the separation process of the liner from the shell or molded article, the liner may be reused in the process again.

FIGS. 8-13 illustrate an alternative mold 200 for a rotational molding system, such as that described with reference to FIG. 7, which can be used to form implant shells of the present invention. As in the earlier embodiment, the mold 200 comprises a top mold piece 202 and bottom mold piece 204 held together by bolts 206 across respective flanges 208, and an inner liner 210 illustrated in cross-section in FIG. 9. Again, the presence of the inner liner 210 is a significant advantage because the implant shells may be formed without a seam that otherwise would result at the intersection of the two mold pieces 202, 204. Desirably, the mold pieces 202, 204 are formed of a metal such as aluminum, and the inner liner 210 is formed of a non-adherent material such as Teflon, for instance ETFE (ethylene-tetrafluoroethylene).

In contrast to the earlier-described embodiment, the inner liner 210 is intended to be reused every time a prosthetic implant shell is formed by the mold. The inner liner 210 remains within the cavity formed by the mold pieces 202, 204, and thus defines the inner surface of the mold 200, during the formation of a number of implants. Preferably the inner liner 210 may remain within the mold pieces 202, 204 for hundreds of uses. As with the earlier-described embodiment, the inner liner 210 is initially formed by rotational molding by injecting free-flowing liner material within the mold pieces 202, 204.

The mold 200 functions much like the aforementioned two-piece case mold 120, in that it includes a relatively large circular opening 212 within a lower flange 214 through or into which inserts a sprue tube (such as the sprue tube 145 of FIG. 7). Although not shown, the sprue tube defines a hollow bore that provides a passage for materials to enter into the mold 200 for forming a prosthetic implant shell, and for solvents or other gases to escape. The preferred implant materials are described above. Although the mold 200 may be used to form a layered shell, the preferred embodiment is to form a single layer implant shell. Once again, however, a single layer implant shell may be formed in multiple steps by a sequence of thin layers such that the finished product exhibits no distinct layers and the entire shell wall is homogenous or uniform in composition. The specific steps for using the mold 200 to form implant shells will not be described further herein as they are essentially the same as previously described with respect to the system of FIG. 7.

Another difference in the mold 200 with comparison to the earlier mold 120 is its relatively thinner wall thickness such that the exterior shape substantially mirrors the interior molded article shape. This design improves the heat transfer properties of the mold 200 such that the uniformity of the temperature at the inner wall, or at the inner liner 210, may be better controlled.

FIGS. 10-13 illustrate several steps in the formation of the mold 200. FIG. 10 illustrates a liner plug or sprue tube 220 exploded below the two mold parts 202, 204. FIG. 11 is a close-up of the lower end of the mold 200 with the liner sprue tube 220 closely fitted within the circular opening of the lower flange 214. The liner sprue tube 220 defines a central through-bore 222 through which liner material may pass and gases vent during formation of the inner liner 210. Additionally, a secondary sprue tube 224 tube that extends into the mold cavity is preferably used to help prevent material from exiting the mold cavity. FIG. 11 illustrates the inner liner 210 after formation.

After formation of the inner liner 210, the liner sprue tube 220 is removed. FIG. 12 illustrates a neck of the mold 200 after boring a tubular neck opening through the liner material from the inside. That is, a small annular section 230 seen in FIG. 11 is removed to form the neck opening having a diameter A. In an exemplary embodiment, the diameter A is between about 2.413-2.540 cm (0.950-1.000 inches). FIG. 13 is a close-up of one corner 232 of the neck opening formed by the liner material 210. The liner material is bored in such a way that the corner 232 is square and closely fits around a sprue tube used to form the implant prosthesis.

For breast implants, the formed shell is ready for further assembly or processing consistent with the usual manner in creating a final breast implant product. For example, a patch over the hole left by the sprue is installed. Ultimately, the implant shell is filled with a filler material of silicone gel or other biocompatible gel material well known to those of skill in the art.

Although the invention has been described and illustrated with a certain degree of particularity, it is understood that the present disclosure has been made only by way of example, and that numerous changes in the combination and arrangement of parts can be resorted to by those skilled in the art without departing from the scope of the invention, as hereinafter claimed.

What is claimed is:

1. A gel-filled soft prosthetic implant, comprising:
a core comprising silicone gel; and
a flexible shell including a substantially homogenous layer of a silicone elastomer comprising a polysiloxane backbone and having a mole percent of at least about 10% of a pendant chemical group that sterically retards permeation of said silicone gel through the layer;
the substantially homogenous layer enveloping and in direct contact with the silicone gel of the core;
wherein the substantially homogenous layer is substantially saturated with the silicone gel.

2. The implant of claim 1 wherein said silicone elastomer comprises a polymer comprising dimethyl siloxane units interspersed with sufficient diphenyl siloxane to provide said pendant chemical group.

3. The implant of claim 2 wherein the mole percent of said diphenyl siloxane units is less than about 25%.

4. The implant of claim 3 wherein the mole percent of said diphenyl siloxane units is about 15%.

5. The implant of claim 1 wherein the shell is substantially entirely defined by said homogenous layer of a silicone elastomer.

6. The implant of claim 1 wherein the shell includes at least one additional layer overlying and enveloping said substantially homogenous layer.

7. The implant of claim 1 wherein the silicone elastomer is a polydimethyl siloxane substituted with said pendant chemical group that sterically retards permeation of said silicone gel through the shell.

8. The implant of claim 7 wherein the pendant chemical group is selected from the group consisting of a phenyl group, a trifluoropropyl group and mixtures thereof.

9. The implant of claim 7 wherein the pendant chemical group is selected from the group consisting of a diphenyl group, a methyl-phenyl group, a trifluoropropyl group and mixtures thereof.

10. The implant of claim 7 wherein the pendant chemical group is a phenyl group.

11. The implant of claim 7 wherein the pendant chemical group is a diphenyl group.

12. The implant of claim 11 wherein the mole percent of the diphenyl group is less than about 25%.

13. The implant of claim 11 wherein the mole percent of the diphenyl group is about 15%.

14. The implant of claim 1 wherein the shell has a substantially uniform thickness of about 0.3 mm.

15. The implant of claim 1, wherein the shell has a strength as saturated with said gel, that is at least as great as its strength in the absence of said gel.

16. The implant of claim 1 wherein the shell has a bleed rate that is less than the bleed rate of a shell having a three layer structure consisting of an intermediate silicone elastomer layer with 15 mole percent of the diphenyl group sandwiched between two silicone elastomer layers with 5 mole percent or less of the diphenyl group.

17. A gel-filled soft prosthetic implant, comprising:
a core comprising silicone gel; and
a flexible shell enveloping and substantially saturated with the silicone gel;
the shell comprising a single, substantially homogeneous silicone elastomer layer comprising a polymer having a polysiloxane backbone and having a minimum mole percent of at least about 10% of a diphenyl group.

18. The implant of claim 17 wherein the shell has a bleed rate that is less than the bleed rate of a shell having a three layer structure consisting of an intermediate silicone elastomer layer with 15 mole percent of the diphenyl group sandwiched between two silicone elastomer layers with 5 mole percent or less of the diphenyl group.

19. The implant of claim 17 wherein the silicone elastomer is a polymer comprising dimethyl siloxane units interspersed with diphenyl siloxane units.

20. A silicone gel-filled soft prosthetic implant, comprising:
a silicone gel; and
a flexible shell containing the silicone gel and defined by a substantially homogeneous layer of a polydimethyl siloxane material having a mole percent of about 15% of a diphenyl group, the layer being in direct contact with the silicone gel and the material having a strength as saturated with said gel that is at least as great as the strength of a substantially identical material in the absence of said gel;
wherein the substantially homogenous layer is substantially saturated with the silicone gel.

21. A gel-filled soft prosthetic implant, comprising:
a core comprising silicone gel; and
a flexible shell including a substantially homogenous layer of a silicone elastomer comprising a polysiloxane backbone and having a mole percent of at least about 10% of a pendant chemical group that sterically retards permeation of said silicone gel through the layer;
wherein the substantially homogenous layer makes up at least about 20% of the thickness of the shell;
further wherein the substantially homogenous layer is substantially saturated with the silicone gel.

22. The implant of claim 21 wherein the substantially homogenous layer comprises a polydimethyl siloxane having a mole percent of at least about 15% of a diphenyl group.

23. The implant of claim 22 wherein the substantially homogeneous layer makes up at least about 50% of the thickness of the shell.

24. The implant of claim 23 wherein the substantially homogeneous layer makes up at least about 90% of the thickness of the shell.

* * * * *

UNITED STATES PATENT AND TRADEMARK OFFICE
CERTIFICATE OF CORRECTION

PATENT NO.        : 8,043,373 B2
APPLICATION NO.   : 12/179340
DATED             : October 25, 2011
INVENTOR(S)       : David J. Schuessler et al.

It is certified that error appears in the above-identified patent and that said Letters Patent is hereby corrected as shown below:

In column 3, line 47, delete "the" and insert -- The --, therefor.

In column 8, line 59, delete "flouro" and insert -- fluoro --, therefor.

In column 9, line 55, after "other" delete "a".

In column 9, line 57, delete "IV." and insert -- IV, --, therefor.

In column 9, line 36, delete "For example, a mole percent of about 15% of the substituted phenyl groups allows a lower degree of saturation because the higher, or more preferably about 13% or".

Signed and Sealed this
Nineteenth Day of June, 2012

David J. Kappos
*Director of the United States Patent and Trademark Office*